United States Patent
Mali et al.

(10) Patent No.: US 6,617,338 B2
(45) Date of Patent: Sep. 9, 2003

(54) ORALLY ADMINISTRABLE ACID STABLE ANTIULCER BENZIMIDAZOLE DERIVATIVES

(75) Inventors: Subhash Mali, Navi Mumbai (IN); Rajan Gupte, Navi Mumbai (IN); Jayant Deshpande, Navi Mumbai (IN); Kamlesh Ranbhan, Navi Mumbai (IN)

(73) Assignee: Kopran Research Laboratories Limited, Maharashtra (IN)

( * ) Notice: Subject to any disclaimer, the term of this patent is extended or adjusted under 35 U.S.C. 154(b) by 0 days.

(21) Appl. No.: 09/964,442

(22) Filed: Sep. 28, 2001

(65) Prior Publication Data

US 2003/0023091 A9 Jan. 30, 2003

Related U.S. Application Data

(63) Continuation of application No. PCT/IN00/00016, filed on Feb. 24, 2000.

(51) Int. Cl.[7] .................. A61K 31/44; C07D 401/00
(52) U.S. Cl. ..................... 514/339; 546/273.7
(58) Field of Search ................. 546/273.7; 514/339

(56) References Cited

U.S. PATENT DOCUMENTS

| | | | |
|---|---|---|---|
| 4,045,563 A | 8/1977 | Berntsson et al. ........... 420/263 |
| 4,587,046 A | 5/1986 | Goodman et al. | |
| 5,037,883 A | 8/1991 | Kopecek et al. | |
| 5,039,806 A | 8/1991 | Brändström et al. | |
| 5,510,418 A | 4/1996 | Rhee et al. | |
| 5,783,178 A | 7/1998 | Kabanov et al. | |
| 5,889,078 A | 3/1999 | Kuzuya et al. | |
| 5,948,773 A | 9/1999 | Akiyama et al. | |
| 5,976,527 A | 11/1999 | Siol et al. | |

FOREIGN PATENT DOCUMENTS

| | | |
|---|---|---|
| EP | 0176308 | 4/1986 |
| EP | 0045200 | 3/1988 |
| WO | 91/19711 | 12/1991 |
| WO | 94/27988 | 12/1994 |
| WO | 95/32957 | 12/1995 |
| WO | 99/63940 | 12/1999 |

OTHER PUBLICATIONS

"Studies on (H+–K+)–ATPase Inhibitors of Gastric Acid Secretion. Prodrugs of 2–[(2–Pyridinylmethyl)sulfinyl]benzimidazole Proton–Pump Inhibitors", J. Med. Chem., vol. 34, pp. 1049–1062, 1991.*

John C. Sih et al., "Studies on (H+–K+)–ATPase Inhibitors of Gastric Acid Secretion. Prodrugs of 2–[(2–Pyridinylmethyl)sulfinyl]benzimidazole Proton–Pump Inhibitors", Journal of Medicinal Chemistry, vol. 34, No. 2, pp. 1049–1062 (1991).

Colin G. Pitt et al., "Sustained Drug Delivery Systems. I. The Permeability of Poly(e–Caprolactone), Poly(DL–Lactic Acid), and Their Copolymers", Journal of Biomedical Materials Research, vol. 13, pp. 497–507, (1979).

D. Puttnam et al., "Polymer Conjugates with Anticancer Activity", Advances in Polymer Science, vol. 122, pp. 55–123 (1995).

* cited by examiner

Primary Examiner—Alan L. Rotman
Assistant Examiner—Binta Robinson
(74) Attorney, Agent, or Firm—Greenblum & Bernstein, P.L.C.

(57) ABSTRACT

Orally administrable acid stable anti-ulcer benzimidazole derivatives which are polymer based. The process of preparation comprises condensing a benzimidazole with a biocompatible partially orally biodegradable synthetic cross linked polymer in aqueous medium at 5–80° C. and pH 4–11 under inert atmosphere. The weight percentage of benzimidazole with respect to the polymeric benzimidazole is 1–50. The reaction mixture is cooled and the product is isolated and dried at 25–45° C. There is also provided a formulation of the polymeric benzimidazoles in combination with pharmaceutically acceptable excipients.

17 Claims, No Drawings

ORALLY ADMINISTRABLE ACID STABLE ANTIULCER BENZIMIDAZOLE DERIVATIVES

"This is a continuation of International Application No PCT/IN 00/00016, filed Feb. 24, 2000, the contents of which are expressly incorporated by reference herein in its entirety. The International Application is not published and will be published under PCT Article 21(2) in English."

TECHNICAL FIELD

The benzimidazole derivatives are polymeric benzimidazoles of the formula I:

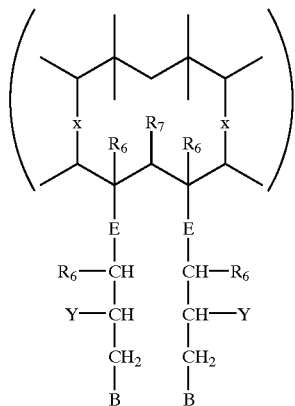

Formula I wherein $R_6$=H or $CH_3$, X=—$OCOCH_2COO$—,

or —$CONHCH_2NHCO$—, $R_7$=H, $CH_3$, $C_2H_5$ or $CONH_2$, Y=OH or $NH_2$, E=—COO—, B is benzimidazole moiety of the formula IIA:

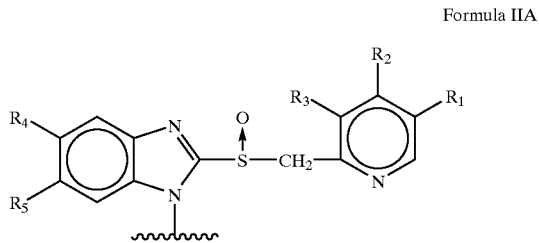

Formula IIA wherein each of $R_1$, $R_2$, $R_3$, $R_4$, $R_5$=H, $C_{1-12}$ alkyl, $C_{6-12}$ (un)substituted aryl, $C_{1-8}$ alkoxy, $C_{6-12}$ aryloxy, $C_{1-5}$ alkoxy carbonyl, $C_{6-12}$ aryloxy carbonyl, $C_{1-5}$ alkoxy alkyl, $C_{6-12}$ alkoxyaryl, $C_{1-5}$ haloalkyl, $C_{1-5}$ alkyl, $C_{1-5}$ haloalkoxyl alkyl or $C_{6-12}$ aryl thioethers, (un) substituted amines or diamines, (un) substituted amides, halo, cyano, nitro, carboxylic acid or carbocyclic or O, N, S containing heterocyclic ring systems or enantiomers thereof.

This invention also relates to pharmaceutically acceptable acid addition salts of the acid stable antiulcer polymeric benzimidazoles, process for the preparation thereof and formulation comprising the same.

The compounds of the invention on oral administration inhibit exogenously or endogenously stimulated gastric acid secretion and thus may be used in the treatment/prevention of peptic ulcers, gastro intestinal inflammatory diseases like duodenal/gastric ulcer or gastritis or other gastro intestinal disorders.

BACKGROUND ART

Antiulcer benzimidazoles of the formula II:

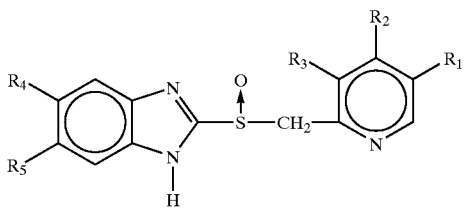

Formula II wherein each of $R_1$, $R_2$, $R_3$, $R_4$, $R_5$ is as defined above, are known to be unstable at neutral or acidic pH of the gastric fluid and undergo decomposition in gastrointestinal fluid on oral administration resulting in loss of activity. Therefore, these compounds are not directly orally ingested. Instead, they are formulated for use by enteric coating or by N-substitution with non-polymeric substituents followed by enteric coating [U.S. Pat. Nos. 4,045,563, 5,039,806 and 5,948,773, PCT Publications Nos WO 95/32957, WO 94/27988 and WO 91/19711, EP Patents Nos 176308 and 0045200 and J. Med. Chem., 34,1049(1991) John Sih et al].

Enteric coated formulations in the form of tablet comprise an initial barrier coating on the active with polymers such as hydroxy propyl methyl cellulose, polyvinyl pyrrolidone or the like, followed by acid resistant coating with polymers such as cellulose acetate phthalate, hydroxy propyl methyl phthalate, polyvinyl acetate phthalate or copolymer of methacrylic acid and ethyl acrylate. The method of preparing enteric coated tablets involves provision of multiple coatings and numerous unit operations such as communition, blending, pelletisation, pan coating, drying, spray coating and/or fluid bed coating/drying because of which it is cumbersome, time consuming and expensive. Benzimidazole actives being sensitive to light, moisture and organic solvents such as dichloromethane acetone or isopropyl alcohol, there are chances of decomposition of the actives during pelletisation thereof. The biologically active compound from such enteric coated formulation is directly released in neutral pH in the intestinal fluid bypassing contact with acidic gastric fluid, where a good percentage of the active is decomposed due to its instability in neutral pH. Thus the bioavailabilty of benzimidazole actives from enteric coated formulations thereof is low. Anti-ulcer benzimidazoles are not known or reported to have been formulated into other oral dosage forms such as syrup or suspension.

Bioactives other than benzimidazoles covalently conjugated with synthetic polymers directly or through a reactive functional group are known and reported. For example, progesterone has been conjugated with aliphatic polyesters such as poly-(ε-Caprolactone), poly-[ε-(+,−)-Calactone], polypivlolactone and poly-(+,−)-dilactide through an ester linkage [(Biomed. Mater. Res, Pitt et al, 1979, 13, 497); (Polymer conjugates with Anticancer Activity, Advances in Polymer Science, D Putnam et al, 1995, Vol 122, page 55–123, Springer Verlag Berline)]. These polymer-conjugates are administered by subdermal route.

U.S. Pat. No 4,587,046 describes covalent conjugation of nearly occuring catecholamines and autocoid moieties with monodisperse amino acid polymers or peptides having an alkyl group through ester/amide linkages. These conjugates are administered parenterally.

U.S. Pat. No. 5,783,178 describes conjugation of actives like vinca alkaloids, mitomycins, bleomycins, fluconazole, amphotericin B, paclitaxel derivatives, cytokines, erythroprotein or polynucleotides with block copolymer of ethyleneoxy monomer or a mixture of ethyleneoxy and the —OCH(CH$_3$)CH$_2$— monomers through bifunctional linking group. This system is mainly used as targeted drug delivery system.

U.S. Pat. No. 5,510,418 describes covalent conjugation of glycosaminoglycan with polyethylene glycol through an ether linkage and is useful for hard/soft tissue augmentation. These polymer-conjugates are to be administered by parenteral route.

Biphenylamine derivatives have been conjugated with polymethacrylic acid. Release of the biphenyl amine derivative from the conjugate was reported only after intraperitoneal injection.

U.S. Pat. No. 5,889,078 describes conjugates of biologically active compounds such as cytostatic fluoro uracil with homopolymer of acrylic acids through ester or amide linkages. These polymer conjugates are mainly used as drug delivery system by parenteral route wherein the polymeric backbone after release of the bioactives is difficult to be excreted from the biological system.

U.S. Pat. No. 5,037,883 describes conjugate of active such as anticancer daunomycin with copolymer of N-(2-hydroxypropyl) acrylamide, N-methacrylamide, N-methacrylic acid and/or N-methacryloylated amino acid through peptide group. These polymer-conjugates are administered by parenteral route.

U.S. Pat. No. 5,976,527 describes conjugates of proteins such as albumin, immunoglobulins, blood clotting factors and peptide hormones with polmethylmethacrylate or polymeth acrylamide comprising reactive oxirane groups, which after immobilisation are used for interaction with biological systems. These conjugate systems are mainly used for diagnostic purposes and as sorbents for pollutants.

Benzimidazole compounds substituted with polymer at the nitrogen thereof are not known or reported.

OBJECTS OF INVENTION

An object of the invention is to provide orally administrable acid stable anti-ulcer benzimidazole derivatives and pharmaceutically acceptable salts thereof, having increased bioavailability.

Another object of the invention is to provide orally administrable acid stable anti-ulcer benzimidazole derivatives and pharmaceutically acceptable salts thereof, which are not enteric coated.

Another object of the invention is to provide orally administrable acid stable anti-ulcer benzimidazole derivatives and pharmaceutically acceptable salts thereof, which have activity comparable to unsubstituted benzimidazoles.

Another object of the invention is to provide orally administrable acid stable anti-ulcer benzimidazole derivatives and pharmaceutically acceptable salts thereof which are capable of being clinically used.

Another object of the invention is to provide a process for the preparation of orally administrable acid stable anti-ulcer benzimidazole derivatives and pharmaceutically acceptable salts thereof which results in products having increased bioavailabilty.

Another object of the invention is to provide a process for the preparation of orally administrable acid stable anti-ulcer benzimidazole derivatives and pharmaceutically acceptable salts thereof, which results in products that are not enteric coated and is therefore simple, less time consuming, less expensive, easy and convenient to carry out.

Another object of the invention is to provide a process for the preparation of orally administrable acid stable anti-ulcer benzimidazole derivatives and pharmaceutically acceptable salts thereof, which results in products having activity comparable to the unsubstituted benzimidazoles.

Another object of the invention is to provide a process for the preparation of orally administrable acid stable anti-ulcer benzimidazole derivatives and pharmaceutically acceptable salts thereof, which results in products capable of being used clinically.

Another object of the invention is to provide a formulation of orally administrable acid stable anti-ulcer benzimidazole derivatives and pharmaceutically acceptable salts thereof, having increased bioavailability.

Another object of the invention is to provide a formulation of orally administrable acid stable anti-ulcer polymeric benzimidazoles and pharmaceutically acceptable salts thereof, which are not enteric coated.

Another object of the invention is to provide a formulation of orally administrable acid stable anti-ulcer benzimidazole derivatives and pharmaceutically acceptable salts thereof, which have activity comparable to the unsubstituted benzimidazoles.

Another object of the invention is to provide a formulation of orally administrable acid stable anti-ulcer benzimidazole derivatives and pharmaceutically acceptable salts thereof, which are capable of being used clinically.

DISCLOSURE OF THE INVENTION

According to the invention there is provided orally administrable acid stable anti-ulcer benzimidazole derivatives of the formula I:

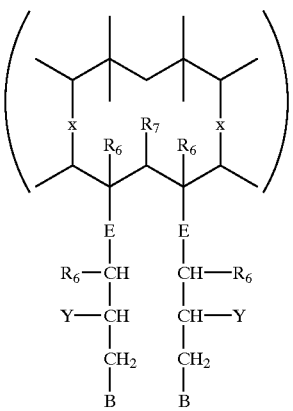

Formula I wherein R$_6$=H or CH$_3$, X=—OCOCH$_2$COO—,

or —CONHCH$_2$NHCO—, R$_7$=H, CH$_3$, C$_2$H$_5$ or CONH$_2$, Y=OH or NH$_2$, E=—COO—, B is benzimidazole moiety of the formula IIA:

Formula IIA

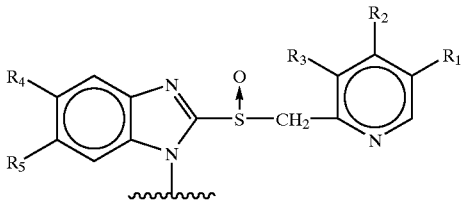

wherein each of R$_1$, R$_2$, R$_3$, R$_4$, R$_5$=H, C$_{1-12}$ alkyl, C$_{6-12}$ (un)substituted aryl, C$_{1-8}$ alkoxy, C$_{6-12}$ aryloxy, C$_{1-5}$ alkoxy carbonyl, C$_{6-12}$ aryloxy carbonyl, C$_{1-5}$ alkoxy alkyl, C$_{6-12}$ alkoxyaryl, C$_{1-5}$ haloalkyl, C$_{1-5}$ alkyl, C$_{1-5}$ haloalkoxy alkyl or C$_{6-12}$ aryl thioethers, (un) substituted amines or diamines, (un) substituted amides, halo, cyano, nitro, carboxylic acid or carbocyclic or O, N, S containing heterocyclic ring systems or enantiomers thereof; and pharmaceutically acceptable acid addition salts thereof.

According to the invention there is also provided a process for the preparation of orally administrable acid stable anti-ulcer benzimidazole derivatives of the formula I:

Formula I

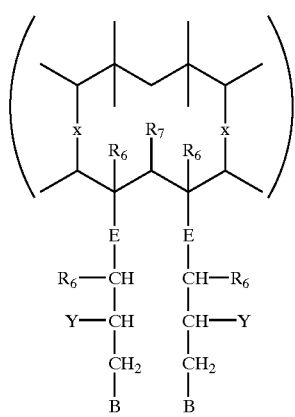

wherein R$_6$=H or CH$_3$, X=—OCOCH$_2$COO—,

or —CONHCH$_2$NHCO—, R$_7$=H, CH$_3$, C$_2$H$_5$ or CONH$_2$, Y=OH or NH$_2$, E=—COO—, B is benzimidazole moiety of the formula IIA:

Formula IIA

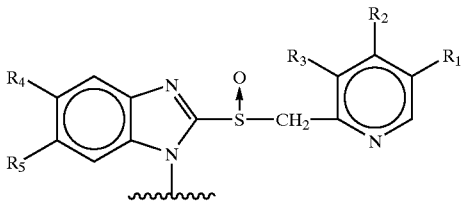

wherein each of R$_1$, R$_2$, R$_3$, R$_4$, R$_5$=H, C$_{1-12}$ alkyl, C$_{6-12}$ (un)substituted aryl, C$_{1-8}$ alkoxy, C$_{6-12}$ aryloxy, C$_{1-5}$ alkoxy carbonyl, C$_{6-12}$ aryloxy carbonyl, C$_{1-5}$ alkoxy alkyl, C$_{6-12}$ alkoxyaryl, C$_{1-5}$ haloalkyl, C$_{1-5}$ alkyl, C$_{1-5}$ haloalkoxy alkyl or C$_{6-12}$ aryl thioethers, (un) substituted amines or diamines, (un) substituted amides, halo, cyano, nitro, carboxylic acid or carbocyclic or O, N, S containing heterocyclic ring systems or enantiomers thereof; and pharmaceutically acceptable acid addition salts thereof, the process comprising:

a) condensing a benzimidazole of the formula II:

Formula II

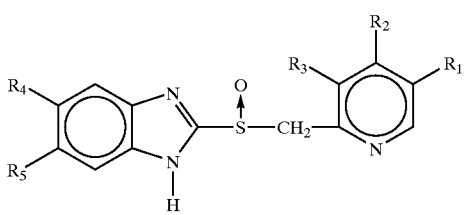

wherein each of R$_1$, R$_2$, R$_3$, R$_4$, R$_5$ is as defined above, with a biocompatible partially orally biodegradable synthetic cross linked polymer of the formula III:

Formula III

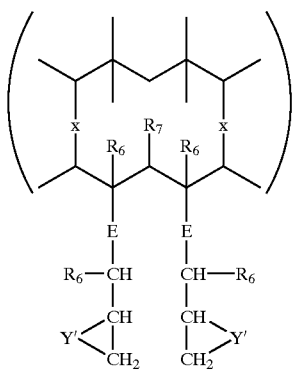

wherein R$_6$, R$_7$, X and E each is as defined above and Y'=O or N, in aqueous medium at 5–80° C. and pH 4–11 under inert atmosphere and stirring; the weight percentage of the benzimidazole with respect to the conjugate being 1–50;

b) cooling, isolating and drying the resulting polymeric benzimidazole at 25–45° C.; and c) if desired, converting the polymeric benzimidazole into pharmaceutically acceptable acid addition salts.

According to the invention, there is also provided a formulation of orally administrable acid stable anti-ulcer benzimidazole derivatives of the formula I:

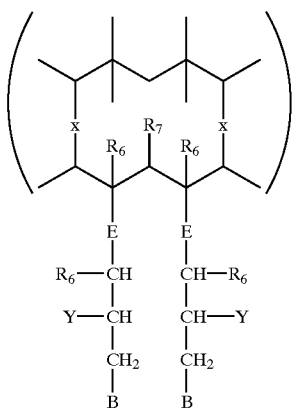

Formula I wherein $R_6$=H or CH$_3$, X=—OCOCH$_2$COO—,

or —CONHCH$_2$NHCO—, $R_7$=H, CH$_3$, C$_2$H$_5$ or CONH$_2$, Y=OH or NH$_2$, E=—COO—, B is benzimidazole moiety of the formula IIA:

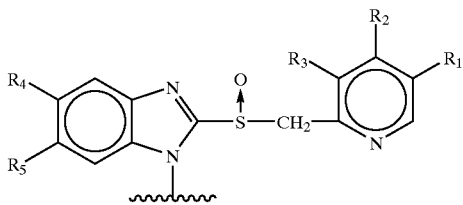

Formula IIA wherein each of $R_1$, $R_2$, $R_3$, $R_4$, $R_5$=H, $C_{1-12}$ alkyl, $C_{6-12}$ (un)substituted aryl, $C_{1-8}$ alkoxy, $C_{6-12}$ aryloxy, $C_{1-5}$ alkoxy carbonyl, $C_{6-12}$ aryloxy carbonyl, $C_{1-5}$ alkoxy alkyl, $C_{6-12}$ alkoxyaryl, $C_{1-5}$ haloalkyl, $C_{1-5}$ alkyl, $C_{1-5}$ haloalkoxy alkyl or $C_{6-12}$ aryl thioethers, (un) substituted amines or diamines, (un) substituted amides, halo, cyano, nitro, carboxylic acid or carbocyclic or O, N, S containing heterocyclic ring systems or enantiomers thereof; and pharmaceutically acceptable acid addition salts thereof, in combination with pharmaceutically acceptable excipients.

The compounds of the formula II may be racemic or enantiomeric.

Preferably the compound of the formula II may be 5-methoxy-2[(4-methoxy-3,5-dimethyl-2-pyridinyl) sulfinyl]-1H-benzimidazole i.e. omeprazole, wherein $R_1$=CH$_3$, $R_2$=OCH$_3$, $R_3$=CH$_3$, $R_4$=OCH$_3$, $R_5$=H; or 5-(difluoro methoxy)-2-[[(3,4-dimethoxy-2-pyridinyl) methyl]sulfinyl]-1H-benzimidazole ie pantoprazole, wherein $R_1$=H, $R_2$=OCH$_3$, $R_3$=OCH$_3$, $R_4$=OCHF$_2$, $R_5$=H; or 2[[[3-methyl-4-(2,2,2-trifluoroethoxy)-2-pyridinyl] methyl]sulfinyl]-1H-benzimidazole ie lansoprazole, wherein $R_1$=H, $R_2$=OCH$_2$CF$_3$, $R_3$=CH$_3$, $R_4$=H, $R_5$=H.

The polymers may be formed in known manner by polymerisation of monomers such as acrylic acid, substituted acrylic acids, acrylamide, substituted acrylamides, acrylonitrile, substituted acrylontriles, esters of acrylic or substituted acrylic acids, styrene, vinyl styrene, vinyl anhydride or derivatives thereof, preferably acrylic acid, methacrylic acid, acrylamide, methacrylaide, acrylonitrile, ethyl acrylate, methyl acrylate, butyl acrylate, hydroxyethylmethyl acrylate or 2-hexylethylmethacrylate.

Preferably Y' in the polymer of the formula III is oxygen atom and Y in the polymeric benzimidazole of the formula 1 is hydroxyl group.

Pharmaceutically acceptable acid addition salts of the conjugate may be hydrochloride, hydrobromide, hydroiodide, sulfate, phosphate, nitrate, perchlorate, formate, acetate, propionate, succinate, glycolate, lactate, tartarate, citrate, ascorbate, piruvate or alginate prepared in a known manner by treating the polymeric benzimidazole with acid such as hydrochloric acid, hydrobromic acid, hydroiodic acid, sulphuric acid, phosphoric acid, nitric acid, perchloric acid, formic acid, acetic acid, propionic acid, succinic acid, glycolic acid, lactic acid, tartaric acid, citric acid, ascorbic acid, pyruvic acid, or alginic acid respectively.

The weight percentage of the benzimidazole of the formula II may be preferably 20% with respect to the conjugate.

The condensation pH may be preferably 6–11.

The temperature for condensation may be preferably 10–40° C.

Isolation of the polymeric benzimidazole may be by filtration, decantation or centrifugation, preferably filtration.

The polymeric benzimidazole may be dried in a tray dryer or vacuum tray dryer, preferably tray dryer, preferably at 30–50° C.

The excipients may be lactose, magnesium stearate, methyl cellulose, distilled water, microcrystalline cellulose, maltodextrin, glycerin, flavouring agents or other excipients known in the art.

The polymeric benzimidazoles of the invention are novel and are found to be acid stable due to the polymeric N-substitution. Therefore, they do not disintegrate in the gastrointestinal fluid and are suitable for oral administration without enteric coating. Since they do not disintegrate in the gastrointestinal fluid, their bioavailability is increased as compared to enteric coated benzimidazoles and their activities are comparable to those of unsubstituted benzimidazoles. Because the process for the preparation of the compounds of the invention eliminates enteric coating, it is simple, less time consuming, less expensive, easy and convenient to carry out. Upon oral administration, under the influence of enzymes/chemicals in the gastrointestinal fluid, the polymeric benzimidazole cleaves at the hydrolysable group (E) to release a N-substituted benzimidazole derivative (ie the benzimidazole along with a part of the polymer) having anti-ulcer activity. The remaining part of the polymer is inert, non-toxic and non-absorbable in the gastro intestinal fluid and is excreted from the body as such or as nonabsorbable metabolites thereof. Therefore the polymeric benzimidazole conjugates of the invention are safe for clinical use. The polymeric benzimidazoles of the invention may be formulated into tablets or capsules besides other oral dosage forms such as syrup or suspension.

The following experimental examples are illustrative of the invention but not limitative of the scope thereof.

EXAMPLE 1

The copolymer (5.0 g) prepared using acrylonitrile, glycidyl acrylate and glycol dimethacrylate was mixed with omeprazole [1.25 g] dissolved in aqueous medium at pH 9.5.

The reaction mixture was stirred at 30° C. for 18 hours. The product was filtered washed with water (100 ml×5) and dried under vacuum at 45° C. for 12 hours to obtain 6.1 g of the polymer-substituted omeprazole.

EXAMPLE 2

The copolymer (5.0 g) prepared using glycidyl methacrylate and acrylamide was mixed with omeprazole (1.25 g) dissolved in aqueous medium at pH 9.8. The reaction mixture was stirred at 30° C. for 18 hours. The product was filtered washed with water (100 ml×5) and dried under vacuum at 45° C. for 12 hours to obtain 5.92 g of the polymer-substituted omeprazole.

EXAMPLE 3

The copolymer (5.0 g) prepared using glycidyl methacrylate and glycol dimethacrylate was mixed with omeprazole (1.25 g) dissolved in aqueous madium at pH 10.4. The reaction mixture was stirred at 30° C. for 18 hours. The product was filtered washed with water (100 ml×5) and dried under vacuum at 45° C. for 12 hours to obtain 6.05 g of the polymer-substituted omeprazole.

EXAMPLE 4

The procedure of Example 2 was followed using omeprazole (2.5 g) and pH 10.2 instead of omeprazole (1.25 g) and pH 9.8 to obtain 6.45 g of the polymer-substituted omeprazole.

EXAMPLE 5

The procedure of Example 3 was followed using omeprazole (2.5 g) instead of omeprazole (1.25 g) to obtain 6.32 g of the polymer-substituted omeprazole.

EXAMPLE 6

The procedure of Example 2 was followed using lansoprazole (3.0 g) instead of omeprazole (1.25 g) to obtain 5.8 g of the polymer-substituted lansoprazole.

EXAMPLE 7

The procedure of Example 2 was followed using pantoprazole (3.0 g) instead of omeprazole (1.25 g) to obtain 5.9 g of the polymer-substituted pantoprazole.

EXAMPLE 8

Tablets containing the following ingredients:

| Tablets containing the following ingredients: | |
|---|---|
| Polymeric benzimidazole of Example 2 | 100.0 g |
| Lactose | 70.0 g |
| Magnesium stearate | 1.5 g |
| Methyl cellulose | 0.6 g |
| Crosspovidone | 5.5 g |
| Distilled water | q.s | were prepared by mixing to form a wet mass and forcing the wet mass through a sieve, granulating and drying on an oven. After drying, the granulate was mixed with crosspovidone and magnesium stearate. The dry mixture was pressed into tablet (1000 tablets) Each tablet containing 100 mg of active substance using 5 mm diameter punches.

EXAMPLE 9

Suspension containing the following ingredients were prepared:

| Suspension containing the following ingredients were prepared: | |
|---|---|
| Polymeric benzimidazole of Example 2 | 2.0 g |
| Glycerin | 55.0 g |
| Pharma grade sugar | 320.0 g |
| Maltodextrin | 0.5 g |
| Flavouring agent | 0.5 g |
| Ethanol | 5.0 ml |
| Distilled water | 100.0 ml |

EXAMPLE 10

| Capsules containing: | |
|---|---|
| Polymeric benzimidazole of Example 2 | 100.0 g |
| Anhydrous lactose | 300.0 g |
| Microcrystalline cellulose | 20.0 g |
| Magnesium sterate | 0.5 g | were mixed in geometrical order using planatory mixer. The blend was sieved and filled into capsules.

Biological activity

Wistar albino rats of either sex, fed on standard rat chow diet were divided into the groups of 10 animals each. The distribution of animals in groups, the sequence of trials and the treatment allotted to each group were randomized. Gastric ulceration was produced by pylorus ligation and absolute ethanol administration. In these methods, animals were fasted for 36 hrs before the experiment. Coprohagy was prevented by fasting the animals in cages with grating as the floor. Duodenal ulceration was produced by cysteamine and in this model fasting is not required and hence food and water were made available as libidum till the start of the experiment. The animals were sacrificed using anaesthetic ether after the completion of experiments; the stomachs were removed, opened along the greater curvature, washed with saline and examined with 6.4* (cm diameter) binocular magnifier. Lesions were assessed by two observers unaware of the experimental protocol.

Drug Treatment Schedule

Drugs used were polymeric benzimidazoles of Examples 1 to 7 (1.5 mg to 10 mg/kg, peroral ie p.o) and unsubstituted and unenteric coated omeprazole (manufactured by us, 0.40 mg/kg p.o). They were administered per orally, 30 minutes after the drug treatment the animals were subjected to any ulcerogenic procedure.

Pylorus Ligated Rats

Rats were anesthetized with anaesthetic ether and the portion of abdomen was opened by a small midline incision below the xiphoid process. Pylorus portion of the stomach was lifted and ligated. During the process care was taken to avoid the traction of the pylorus or damage to its blood supply. The stomach was isolated from the body and its contents were collected, measured and centrifuged. The supernatant was used immediately for biochemical analysis for total acidity. Immediately after the removal of the contents from the stomach, they were examined for lesions in the stomach portion which were measured and expressed in terms of ulcer index calculated as the total ulcerated area divided by the total mucosal area.

Ethanol Induced Gastric Mucosal Damage

Rats were given 1.0 ml of 100% ethyl alcohol (p.o) by gavage needle, 30 minutes after the administration of test compound. Two hours after ethanol administration all rats were sacrificed. The area of the glandular portion of the stomach was measured in millimeters. Then the area of the gastric mucosal damage was calculated in square millimeters and the severity of the gastric mucosal injury was expressed as percentage of the surface area of the glandular stomach.

Cysteamine-HCl induced duodenal ulcers in rats

Wistar albino rats of either sex were used. Food and water were available ad libidum; throughout the study. Duodenal ulcers were induced by two administrations of cysteamine hydrochloride 400 mg/kg p.o, in 10% aqueous solution at an interval of 4 hour. The drugs under study were administered 30 minutes before each dose of cysteamine hydrochloride. All the animals were sacrificed 24 hours after the first dose of cysteamine and duodenum were excised carefully and opened along the antimesenteric side. The mean ulcer area was obtained by measuring the dimensions of the duodenal ulcer(s) in square millimeters.

Results

Effect on Ulcer Index and Total Acid Output in Pylorus Ligated Rats

Pylorus ligation for 19 hours produced accumulation of gastric secretory volume and increase in the total acid output of the gastric juice as shown in Table I.

TABLE 1

Effect of polymeric benzimidazoles of Examples 1 to 7 and omeprazole on total acid output and intensity of gastric lesions in pylorus ligated rats as calculated by [mean + Standard Error Mean ie SEM]

| Polymeric benzimidazole of | mg/kg × days (p.o) | Total acid output meq/L/100 g | Ulcer index |
|---|---|---|---|
| Control | 0 × 0 | 186.41 ± 19.05 | 2.88 ± 0.18 |
| Example 1 | 2 × 1 | 60.5 ± 4.1 | 1.09 ± 0.51 |
|  | 10 × 1 | 71.32 ± 4.5 | 1.15 ± 0.34 |
| Example 2 | 2 × 1 | 65.8 ± 6.3 | 1.28 ± 0.32 |
|  | 10 × 1 | 61.15 ± 6.9 | 1.17 ± 0.42 |
| Example 3 | 2 × 1 | 71.15 ± 2.5 | 1.35 ± 0.37 |
|  | 10 × 1 | 69.81 ± 2.4 | 1.33 ± 0.39 |
| Example 4 | 1.5 × 1 | 72.36 ± 6.81 | 1.18 ± 0.23 |
|  | 10 × 1 | 68.11 ± 6.53 | 1.24 ± 0.39 |
| Example 5 | 1.5 × 1 | 55.14 ± 5.81 | 1.21 ± 0.51 |
|  | 10 × 1 | 54.06 ± 6.52 | 1.15 ± 0.67 |
| Example 6 | 1.5 × 1 | 77.15 ± 6.3 | 1.25 ± 0.45 |
|  | 10 × 1 | 68.53 ± 6.9 | 1.15 ± 0.32 |
| Example 7 | 1.5 × 1 | 59.58 ± 7.19 | 1.41 ± 0.32 |
|  | 10 × 1 | 52.65 ± 5.5 | 1.37 ± 0.51 |
| Omeprazole | 0.4 × 1 | 72.93 ± 7.17 | 0.88 ± 0.10 |

The benzimidazole active content in the compounds of Examples 1 to 7 was 20–30%.

Conclusion:—The results of Table 1 showed that polymeric benzimidazoles of Examples 1 to 7 (both the doses) produced decrease in ulcer index and total acid output. The activities of the polymeric benzimidazoles of Examples 1 to 7 were comparable to those of omeprazole.

Effect on Absolute Ethanol Induced Gastric Mucosal Damage

Oral administration of absolute ethanol produced blackish elongated bands of haemorrhagic lesions in the corpus mucosa along the long axis of the stomach within 2 hours. Polymeric benzimidazoles of Examples 1 to 7 when administered in the doses 1.5 mg to 2 mg/kg p.o decreased the area of gastric mucosal lesions when compared to ethanol treated rats in control, as shown in Table 2.

TABLE 2

Effect of polymeric benzimidazoles of Examples 1–7 on gastric mucosal injury induced by absolute ethanol in 7 rats

| polymeric benzimizole of | (mg/kg × days) (p.o) | Area of gastric lesions (mm$^2$) (% of the glandular stomach) | % of untreated rats |
|---|---|---|---|
| Control | 0 × 0 | 34.62 ± 1.44 | 100 |
| Example 1 | (2 × 1) | 3.85 ± 0.19 | 11.12 |
| Example 2 | (2 × 1) | 4.51 ± 0.22 | 12.99 |
| Example 3 | (2 × 1) | 3.51 ± 0.81 | 10.14 |
| Example 4 | (1.5 × 1) | 1.55 ± 0.6 | 4.48 |
| Example 5 | (1.5 × 1) | 1.73 ± 0.32 | 4.99 |
| Example 6 | (1.5 × 1) | 1.95 ± 0.48 | 5.63 |
| Example 7 | (1.5 × 1) | 1.79 ± 0.32 | 5.17 |

The benzimidazole active content in the compounds of Examples 1 to 7 was 20–30%.

The results of Table 2 were significantly different from those of control conditions as indicated by P<0.05.

Effect on Cysteamine Induced Duodenal Ulcer Model

Administration of cysteamine caused some mortality in rats within 24 hour. The rats when died had perforated ulcers. Polymeric benzimidazoles of Examples 1–7 (1.5 mg and 2 mg/kg) decreased significantly the mean ulcer area when compared to those in rats in control. However mortality was reduced in the animals treated with polymeric benzimidazole of Examples 1 to 7 as shown in Table 3.

Effect of polymeric benzimidazoles of Examples 1–17 on cysteamine induced duodenal ulcer 7 rats models (mean±SEM)

TABLE 3

Effect of polymeric benzimidazoles of Examples 1–7 on cysteamine induced duodenal ulcer 7 rats models: (mean + SEM)

| Polymeric benzimidazole of | (mg/kg × days) (p.o) | Mean Ulcer Area (mm$^2$) |
|---|---|---|
| Control | (0 × 0) | 13.94 ± 1.27 |
| Example 1 | (2 × 1) | 6.55 ± 0.3 |
| Example 2 | (2 × 1) | 7.13 ± 0.43 |
| Example 3 | (2 × 1) | 6.85 ± 0.51 |
| Example 4 | (1.5 × 1) | 6.34 ± 0.62 |
| Example 5 | (1.5 × 1) | 6.13 ± 0.35 |
| Example 6 | (1.5 × 1) | 6.83 ± 0.33 |
| Example 7 | (1.5 × 1) | 6.53 ± 0.47 |

The benzimidazole active content in the compounds of Examples 1 to 7 was 20–30%.

The results of Table 3 were significantly different from those of control conditions as indicated by P<0.05.

Expressions of Results and Statistics

The results were analyzed statistically using the unpaired students T test. The value of P less then 5% (P<0.05) was considered to be statistically significant.

In-vitro digestion of polymeric benzimidazole of Examples 1–5 using simulated gastric and intestinal fluids for 2 and 7 hrs respectively at 37° C., did not show the release of Omeprazole (tested by HPLC procedure given for omeprazole in USP-23). Similarly, polymeric benzimidazoles of Examples 6 and 7 after digestion, did not show release of lansoprazole and pantoprazole (USP-23) respectively. Therefore it should be assumed that the drugs released were derivatives (modified forms) of omeprazole, lansoprazole and pantoprazole respectively.

In-vivo screening of the polymeric benzimidazole of Example 1–7 in rats by pylorus ligation, ethanol induced cytoprotective property and antiduodenal ulcer property reveals significant proton pump inhibiting property at 1.5–2 mg/kg body weight dose.

Conclusions

Polymeric benzimidazoles of Examples 1–7 show significant antiulcer activity in rats in all the three experimental models, viz. pylorus ligated rats, ethanol induced gastric mucosal injury and cysteamine induced duodenal ulcer. Activities were comparable with that of omeprazole in pylorus ligated rats model.

What is claimed is:

1. Orally administrable administrable acid stable anti-ulcer benzimidazole compound of the formula I:

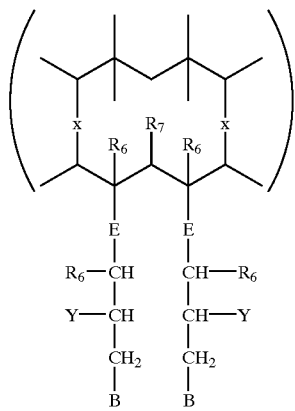

Formula I wherein $R_6$=H or $CH_3$, X=—OCOCH$_2$COO—,

or —CONHCH$_2$NHCO—, $R_7$=H, $CH_3$, $C_2H_5$ or $CONH_2$, Y=OH or $NH_2$, E=—COO—, R is benzimidazole moiety of the formula IIA:

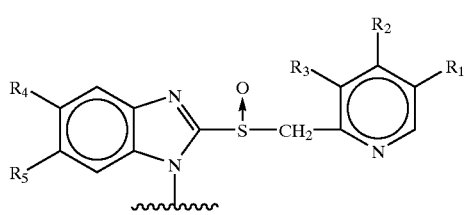

Formula IIA wherein each of $R_1$, $R_2$, $R_3$, $R_4$, $R_5$=H, $C_{1-12}$ alkyl, $C_{1-8}$ (un)substituted aryl, $C_{1-8}$ alkoxy, $C_{6-12}$ aryloxy, $C_{1-5}$ alkoxy carbonyl, $C_{6-12}$ aryloxy carbonyl, $C_{1-5}$ alkoxy alkyl, $C_{6-12}$ alkoxyaryl, $C_{1-5}$ haloalkyl, $C_{1-5}$ alkyl, $C_{1-5}$ haloalkoxy alkyl or $C_{6-12}$ aryl thioethers, (un) substituted amines or diamines, (un)substituted amides, halo, cyano, nitro, carboxylic acid or carbocyclic or enantiomers thereof; or a pharmaceutically acceptable acid addition salt thereof.

2. A polymeric benzimidazole compound as claimed in claim 1, wherein the benzimidazole moiety is omeprazole.

3. A polymeric benzimidazole compound as claimed in claim 1, wherein the benzimidazole moiety is lansoprazole.

4. A polymeric benzimidazole compound as claimed in claim 1, wherein the benzimidazole moiety is pantoprazole.

5. A process for the preparation of orally administrable acid stable anti-ulcer benzimidazole compound of the formula I:

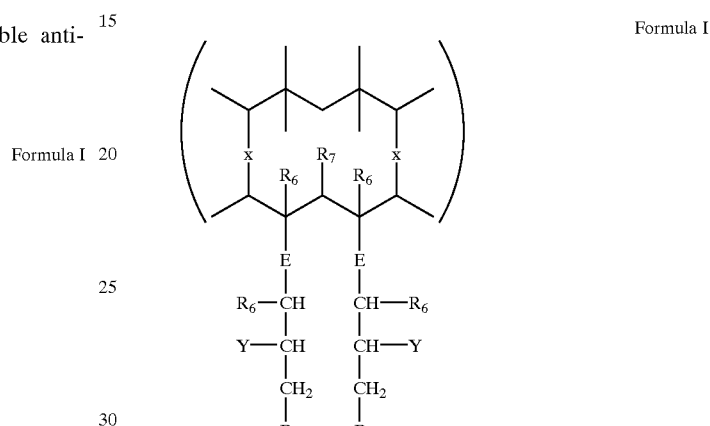

Formula I wherein $R_6$=H or $CH_3$, X='OCOCH$_2$COO—,

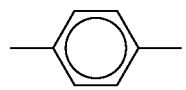

or —CONHCH$_2$NHCO—, $R_7$=H, $CH_3$, $C_2H_5$ or $CONH_2$, Y=OH or $NH_2$, E=—COO—, B is benzimidazole moiety of the formula IIA:

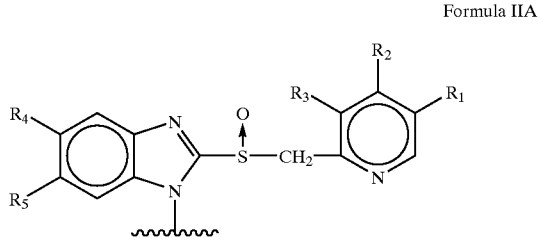

Formula IIA wherein each of $R_1$, $R_2$, $R_3$, $R_4$, $R_5$, $R_5$=H, $C_{1-12}$ alkyl, $C_{6-12}$ (un)substituted aryl, $C_{1-8}$ alkoxy, $C_{6-12}$, aryloxy, $C_{1-5}$ alkoxy carbonyl, $C_{1-5}$, alkoxy carbonyl, $C_{1-5}$ alkoxy alkyl, $C_{6-12}$ alkoxyaryl, $C_{1-5}$ haloalkyl $C_{1-5}$, alkyl, $C_{1-5}$ haloalkoxy alkyl or $C_{6-12}$ aryl thioethers, (un)substituted amines or diamines, (un)substituted, amides, halo, cyano, nitro, carboxylic acid or carbocyclic or enantiomers thereof; or a pharmaceutically acceptable acid addition salt thereof, the process comprising:

a) condensing a benzimidazole of the formula II:

Formula II

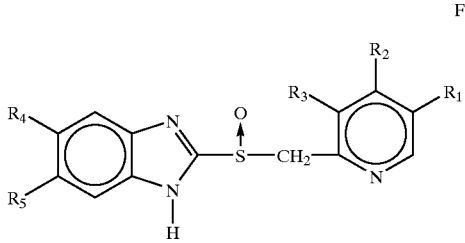

wherein each of $R_1$, $R_2$, $R_3$, $R_4$, $R_5$ is as defined above, with a biocompatible partially orally biodegradable synthetic cross linked polymer of the formula III:

Formula III

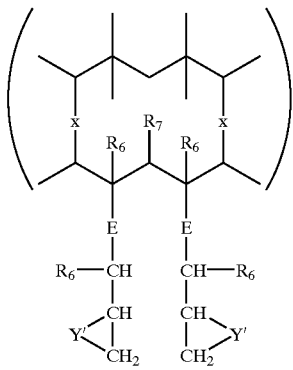

wherein $R_6$, $R_7$, X and E each is as defined above and Y'=O or N, in aqueous medium at 5–80° C. and pH 4–11 under inert atmosphere and stirring; the weight percentage of the benzimidazole with respect to the benzimidazole compound being 1–50;
   b) cooling, isolating and drying the resulting polymeric benzimidazole at 25=45° C.; and
   c) if desired, converting the polymeric benzimidazole into a pharmaceutically acceptable acid addition salt.

6. A process as claimed in claim 5, wherein the benzimidazole is omeprazole.

7. A process as claimed in claim 5, wherein the benzimidazole is lansoprazole.

8. A process as claimed in claim 5, wherein the benzimidazole is pantoprazole.

9. A process as claimed in claim 5, wherein the weight percentage of the benzimidazole with respect to the benzimidazole compound is 20.

10. A process as claimed in claim 5, wherein the condensation temperature is 30° C.

11. A process as claimed in claim 5, wherein the condensation pH is 6–11.

12. A process as claimed in claim 5, wherein the isolation is carried out by filtration.

13. A process as claimed in claim 5 wherein the drying is carried out in a tray dryer at 30–50° C.

14. A composition of an orally administrable acid stable anti-ulcer benzimidazole compound of the formula I:

Formula I

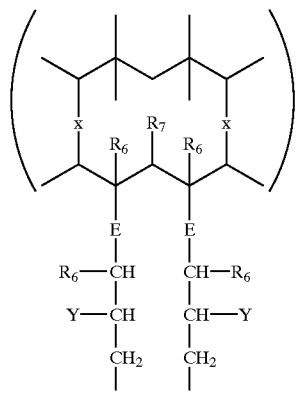

wherein $R_6$=H or $CH_3$, X=—$OCOCH_2COO$—,

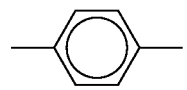

or —$CONHCH_2NHCO$—, $R_7$=H, $CH_3$, $C_2H_5$ or $CONH_2$, Y=OH or $NH_2$, E=—COO—, B is benzimidazole moiety of the formula IIA:

Formula IIA

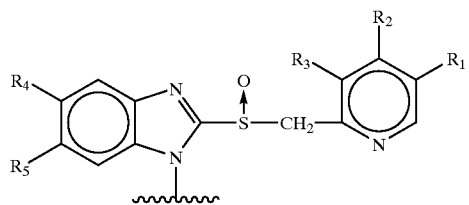

wherein each of $R_1$, $R_2$, $R_3$, $R_4$, $R_5$=H, $C_{1-12}$ alkyl, $C_{6-12}$ (un)substituted aryl, $C_{1-5}$ alkoxy, $C_{6-12}$ aryloxy, $C_{1-3}$ alkoxy carbonyl, $C_{6-12}$ aryloxy carbonyl, $C_{1-5}$ alkoxy alkyl, $C_{6-12}$ alkoxyaryl, $C_{1-5}$ haloalkyl, $C_{1-5}$ alkyl, $C_{1-5}$ haloalkoxy alkyl or $C_{6-12}$ aryl thioethers, (un)substituted amities or diamines, (un)substituted amides, halo, cyano, nitro, carboxylic acid or carbocyclic or enantiomers thereof or a pharmaceutically acceptable acid addition salt thereof, in combination with at least one pharmaceutically acceptable excipient.

15. A composition as claimed in claim 14, wherein the benzimidazole moiety is omeprazole.

16. A composition as claimed in claim 14, wherein the benzimidazole moiety is lansoprazole.

17. A composition as claimed in claim 14, wherein the benzimidazole moiety is pantoprazole.

* * * * *

UNITED STATES PATENT AND TRADEMARK OFFICE
CERTIFICATE OF CORRECTION

PATENT NO.    : 6,617,338 B2
DATED         : September 9, 2003
INVENTOR(S)   : S. Mali et al.

It is certified that error appears in the above-identified patent and that said Letters Patent is hereby corrected as shown below:

Column 13,
Line 16, delete the second occurrence of "administrable".
Line 47, "NH," should be -- $NH_2$, --.
Line 47, "R" should be -- B --.
Line 61, "$C_{1-8}$" should be -- $C_{6-12}$ --.

Column 14,
Line 33, "OCOCH₂COO-" should be -- -OCOCH₂COO- --.
Line 59, "$C_{1-5}$ alkoxy carbonyl" should be -- $C_{6-12}$ aryloxy carbonyl --.

Column 16,
Line 43, "$C_{1-5}$ alkoxy" should be -- $C_{1-8}$ alkoxy --.
Line 43, "$C_{6-12,}$ aryloxy" should be -- $C_{6-12}$ aryloxy --.
Line 43, "$C_{1-3}$ alkoxy carbonyl" should be -- $C_{1-5}$ alkoxy carbonyl --.
Line 47, "amities" should be -- amines --.
Line 49, after "thereof" insert -- ; --.

Signed and Sealed this

Twenty-second Day of June, 2004

JON W. DUDAS
*Acting Director of the United States Patent and Trademark Office*